United States Patent [19]
Grandon

[11] Patent Number: 4,581,032
[45] Date of Patent: Apr. 8, 1986

[54] INTRAOCULAR LENS

[76] Inventor: Stanley C. Grandon, 4529 Tanbark, Bloomfield Hills, Mich. 48013

[21] Appl. No.: 597,353

[22] Filed: Apr. 6, 1984

[51] Int. Cl.⁴ .............................................. A61F 2/16
[52] U.S. Cl. ....................................................... 623/6
[58] Field of Search ............................. 3/13, 1; 623/6

[56]  References Cited
U.S. PATENT DOCUMENTS

| 4,242,760 | 1/1981 | Rainin | 3/13 |
| 4,434,515 | 3/1984 | Poler | 3/13 |
| 4,437,194 | 3/1984 | Hahs | 3/13 |

OTHER PUBLICATIONS

"A Guide for Implantation of the Adaptable Pannu Intraocular Lens", Instructional Brochure by American Medical Optics, 1402 E. Alton Ave., Irvine, CA 92714, 12 pages.

Primary Examiner—Ronald L. Frinks
Attorney, Agent, or Firm—Krass and Young

[57] ABSTRACT

An intraocular lens (IOL) and method of use are provided for implanting with quadrilateral support in the anterior chamber of the eye following cataract extraction.

12 Claims, 5 Drawing Figures

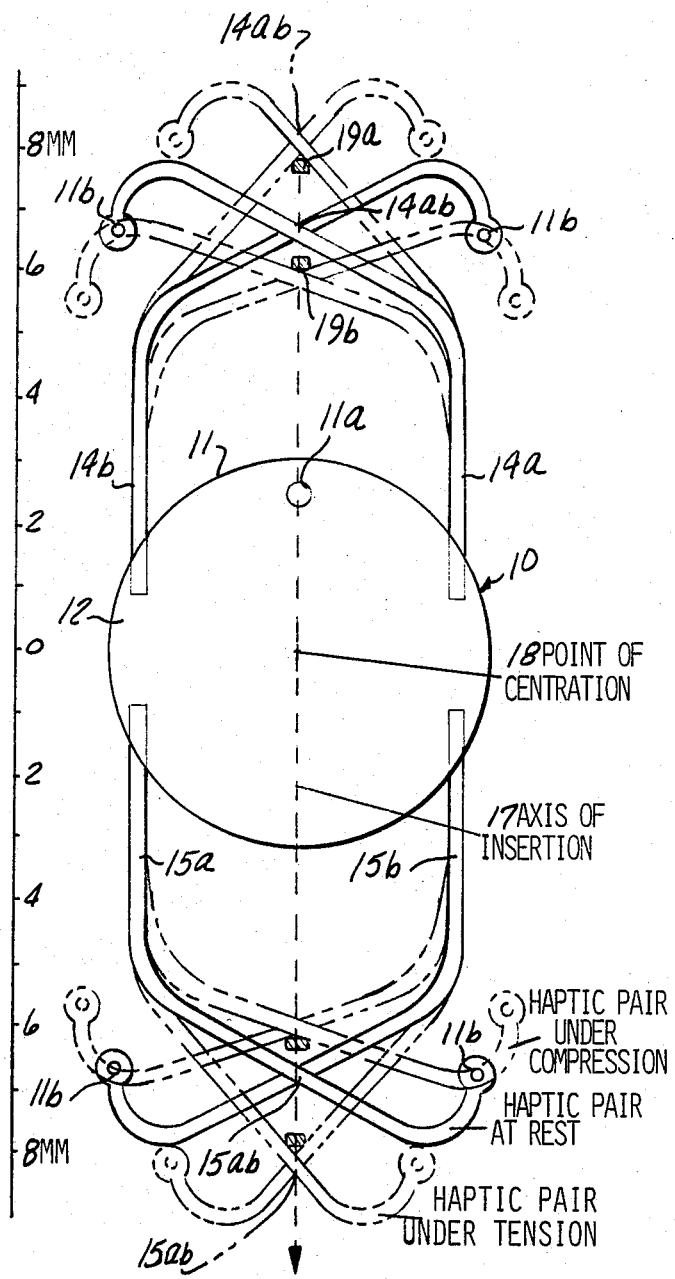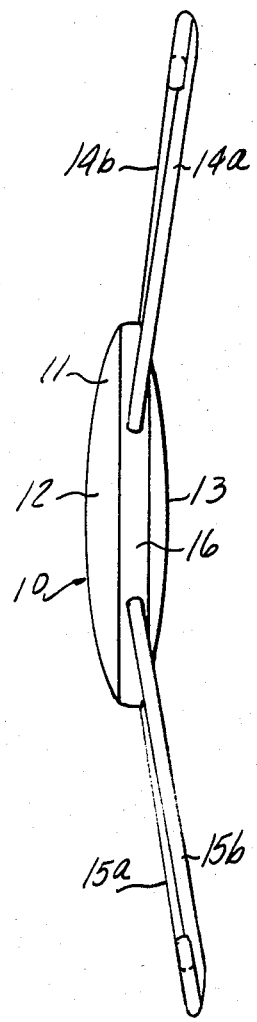
FIG-1
FIG-2

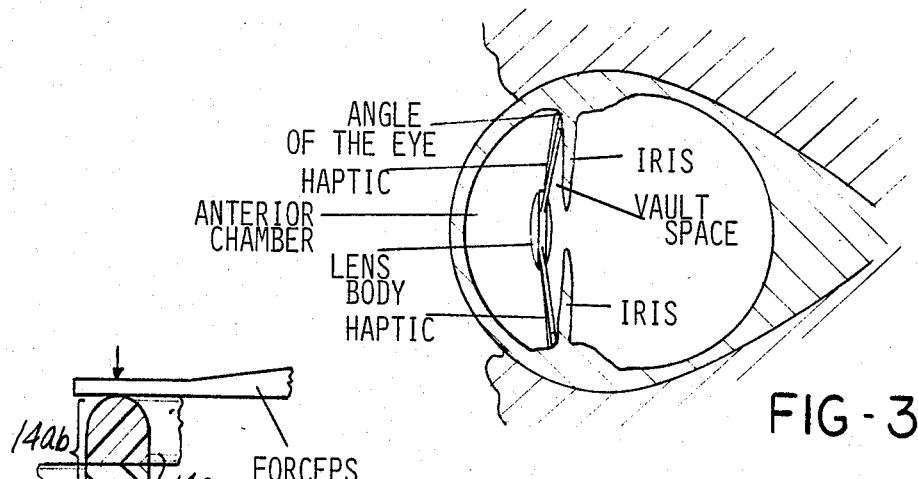
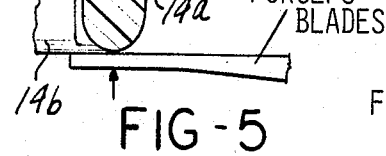
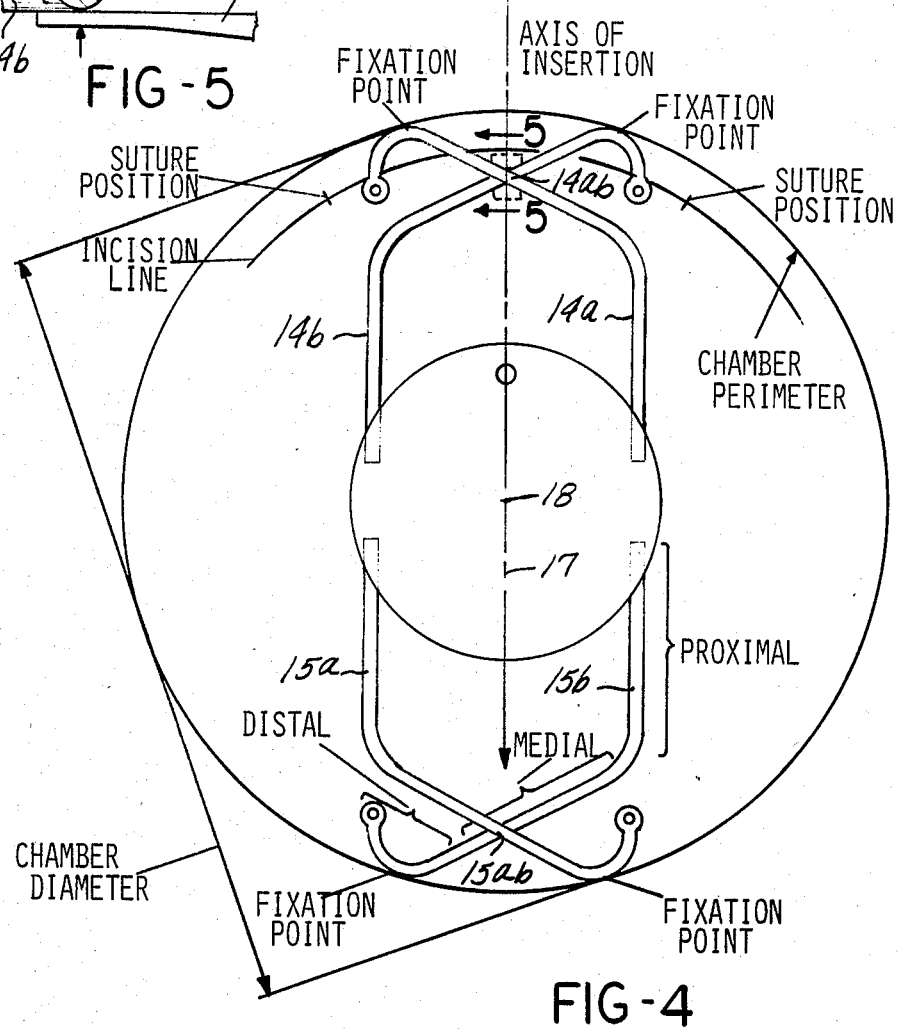

INTRAOCULAR LENS

DESCRIPTION

1. Technical Field

This invention relates to artificial body members and, more particularly, to a unique kind of intraocular lens (IOL) intended to be implanted in the anterior chamber of the eye following cataract extraction.

2. Background Art

Conventional intraocular lenses for the anterior chamber can be described as being generally of three structural types: rigid, semi-flexible, and flexible, the latter including lenses in which the haptic supports especially are flexible. Anterior lenses have several advantages including low dislocation rate, pupil-independence, and low reoperation rate. Disadvantages include risk of exposure to endothelial cell loss, insertion difficulty (as with wide range universal types), lens rotation or propellering, minor malpositioning also known as tucking, globe tenderness, and the requirement for the surgeon to keep an unduly large inventory of lens diameters and dioptric powers.

It is therefore an object of the present invention to provide an improved intraocular anterior chamber lens that overcomes the disadvantages of prior art lenses.

It is another object of the invention to provide a new type of intraocular anterior chamber lens that is compact and can readily be inserted and implanted.

It is still another object of the invention to provide a new anterior lens of the type described that is universal, being disigned in one size for permanent and stable implantation in any of a variety of chamber sizes ranging, for example, from 11.5 mm to 15 mm in diameter.

These and other objects, features and advantages will be seen from the following description and accompanying drawings.

DISCLOSURE OF THE INVENTION

These and other objects are achieved by providing, in one aspect of the invention, an intraocular lens of a novel type presently to be described, that is useful for insertion and implantation in the anterior chamber of the aphakic eye through a surgical incision. The lens has a principal insertion axis and comprises a lens body of given lateral cross-section and radially compressible haptics or loops attached to the lens body for centrally fixating the lens body. The centering means in a preferred embodiment include two bilateral opposed sets of filaments, each filament set comprising a pair of bilaterally symmetrical outwardly extending resilient filaments. Each filament pair in its outward extension is aligned with the insertion axis; each filament of the respective pairs has proximal, medial and distal portions. Each filament is dimensionally stable in a relaxed state and flexes when under tension or under compression. The filament proximal portions are generally parallel to each other and spaced apart at equal distance from the insertion axis. The medial portions of each filament pair cross each other at a point referred to herein as an intersection. The distal portions of the filament pair are configured when implanted, for extensive matching engagement with the respective eye angle, and preferably configured for this purpose in an arcuate segment that is generally congruent with the equitorial curvature of the eye angle. For insertion purposes, the lateral dimension of each filament pair when relaxed substantially matches or is not greater than the lateral dimension of the lens body whereby the centering means can be freely inserted through any surgical incision through which the lens body can be inserted. In other words, the lens can be inserted without having the loops or haptics hang up when the lens body is guided in along its insertion axis to a point of centration in the chamber.

BRIEF DESCRIPTION OF THE DRAWINGS

The invention will be more fully understood by reference to the following detailed description and accompanying drawings in which:

FIG. 1 is a plan view of a preferred embodiment of an intraocular lens according to the invention;

FIG. 2 is a side view in elevation of the intraocular lens of FIG. 1;

FIG. 3 is a view is side elevation of a preferred embodiment of an intraocular lens in situ, the eye being shown in cross-section;

FIG. 4 is a plan view of a preferred embodimen of an intraocular lens shown as implanted in the anterior chamber, according to the invention; and FIG. 5 is a fragmentary view partly in section taken on line 5—5 of FIG. 4.

DESCRIPTION OF PREFERRED EMBODIMENTS AND BEST MODE OF PRACTICING THE INVENTION

The following description concerns preferred embodiments of the invention, for the purpose of illustrating the invention. Thus, this description is to be read broadly and not be taken in a limiting sense.

In the embodiment of FIGS. 1 and 2, the lens 10 includes a lens body 11 having a front face 12 and a rear face 13 as well as flexible top haptic loops 14a and 14b and bottom loops 15a and 15b secured by suitable means such as staking extending outwardly from the edge 16 of the lens body 11. A fenestration 11a ia provided for inserting, manipulating, positioning, suturing or fixating the lens in the anterior chamber (FIG. 3). The haptic loops 14a, 14b, 15a and 15b (referred to herein as filament loops) each comprise a filament that has proximal, medial and distal portions as shown in FIG. 4. The medial portions of the haptic pairs 14a/14b and 15a/15b cross at an intersection 14ab and 15ab respectively. In the preferred embodiment shown in FIG. 1, the end of each filament loop is rounded or otherwise blunted. Each end includes a fenestration 11b which serves as a socket or control surface to receive a surgeon's hook end or other tool surface for guiding, inserting, retracting, narrowing, spreading or otherwise manipulating the respective loops or loop pairs. In a preferred embodiment, the haptic loops are identical in size, shape and resiliency so that the implanted lens has uniform quadrilateral support. The lens 10 has an axis 17 of insertion which in a preferred form is defined by a line or plane passing through the intersections 14ab and 15ab and the centration point 18 of the lens. In a preferred embodiment, the medial portions of the haptic pair are contiguous at their intersection (14ab and/or 15ab, FIGS. 4 and 5). In other preferred embodiments, the filament intersection (14ab and/or 15ab as in FIG. 5) is engageable by the blades of a forceps or other gripping tool, for bilateral or quadrilateral support and manipulation of the lens. In still other preferred forms, the filament intersection is contiguous and engageable by a tension applying tool 19a or compression applying tool 19b (shown in section, FIG. 1) such as a surgeon's hook or probe, to cause the respective haptic pair of an immobilized lens body to move resiliently from its relaxed or at rest position and to assume the position of tension (with narrowing of the distal ends) or the position of compression (with spreading of the distal ends) illustrated in dotted outline in FIG. 1, for purposes to be described presently. The same manipulation to a position of tension or of compression can be achieved using a forceps (as described) instead of a hook or a probe. Preferably, the lens is constructed so that the angle-contacting distal portions of the filament pairs are substantially co-planar. Preferably, the filament pairs have posterior angulation such that the lens, when implanted in the angle of the eye (as shown in FIG. 3), provides a vault space between the lens body and the iris. The lens body and the filaments can be made of any suitable lens material, which material and its construction may be conventional. Commonly used materials which are suitable are medical grade polymethylmethacrylate (PMMA), particularly for the lens body, and polypropylene or PMMA for the filament support structures (e.g., 12-0 transparent polypropylene or equivalent material). For the prevention or control of anterior-posterior movement of the optic or torsional movement and posterior migration of the implanted lens within the anterior chamber, the haptic loops can be suitably structured in ways that per se are art-recognized as, for example, by making the cross-sectional area of the filament proximal and medial portions oblong or semi-oblong (FIG. 5) (and of the distal portion, circular) thereby serving substantially to limit flexion of proximal and medial portions of the filaments to occur only in an axis that is parallel with the lens body, while at the same time maximizing the flexibility and resilience of distal portions for better geometric matching and four-point accomodation to the eye angle.

In another aspect, the invention relates to a method of implanting an anterior chamber intraocular lens of the type described. The method includes the steps of grasping the lens body and at least one filament pair at points in alignment with the insertion axis, and inserting the thus grasped lens through a surgical incision into the anterior chamber in a plane generally parallel to and with vault spacing from the iris plane. For this purpose, the lens while in the relaxed position (FIG. 1) can be grasped in any suitable way, for example, with implant forceps that engages both the lens body 11 adjacent to the fenestration 11a and the filament pair 14a and 14b at the intersection 14ab. Grasping the lens in this way advantageously achieves not only the desired lens alignment but also the desired control of the filament pairs 14a, 14b and 15a, 15b since the spread of their distal portions in the relaxed (at rest, FIG. 1,) position is narrow relative to the sutured incision (FIG. 4) so that the entire lens can easily be accomodated through the incision. In the unlikely circumstance that the spread of the forward filament pair 15a, 15b is too great for the purposes of insertion, the same can be narrowed and the pair 15a, 15b gently slid into the incision by an assisting probe-applied tensioning force of a tool 19a (FIG. 1) at the intersection 15ab. Similar control, if necessary, can be achieved for insertion of the trailing filament pair 14a, 14b by tool engagement at intersection 14ab.

This invention contemplates that the lens, once inserted in the chamber, will be fixated with four-point support in the equitorial zone of the eye angle under compression. To this end, the lens in its unique design is capable of bridging a relatively wide range of chamber diameters. This is illustrated in FIG. 1 where the opposed haptic pairs under compression are positioned to accomodate fixation in a chamber having a diameter of about 14 mm. It will be realized, however, that by varying the degree of compression, the surgeon can accommodate the same size of lens to a range of different diameters so that need for an extensive inventory of lens sizes is avoided. In selecting the lens size for implantation based on preliminary measurement of the eye, the size is selected that will be under compression, as indicated, when fixated. In a preferred embodiment for manipulating the filament pair within the eye angle a tool is appled to the filament pair intersection to cause the distal ends of the filament pair to be brought together or spread apart, as the case may be. Similarly, to enable threading of the trailing distal portion through the incision, the forward distal portion can be placed under compression by a tool-applied force at the intersection 15ab. Once the trailing distal portion is cleared through the incision with the opposing forward distal portion located in the eye angle opposite the incision (e.g., at six o'clock), the compression can be transferred from intersection 15ab to intersection 14ab so that the trailing distal ends can be spread apart and, while centering the lens body in the chamber, supporting the lens by fitting the distal ends within the adjacent eye angle under a state of compression sufficient to maintain centration of the lens body. Positioning and manipulation of the lens can also be achieved by moving and guiding the lens body and/or filaments with a hook tool or other suitable tool inserted in one or more of the fenestrations 11b.

What is desired to claim as my exclusive property in the invention, as described, is the following.

I claim:

1. An intraocular lens having a principal insertion axis and being useful for insertion and implantation in the anterior chamber of the aphakic eye through a surgical incision, comprising a lens body of given lateral cross-section and radially compressible self-centering means attached by staking to the lens body edge for centrally fixating the lens body comprising two bilateral opposed sets of filaments, each filament set comprising a pair of bilaterally symmetrical outwardly extending resilient filaments, each filament pair in its outward extension being aligned with the insertion axis, each filament of the respective pairs having proximal, medial and distal portions, with the filament proximal portions being generally parallel to each other and spaced apart at equal distance from the insertion axis and with the medial portions of each filament pair crossing each other at an intersection, the distal portions being configured when implanted for extensive matching engagement with the respective eye angle, the lateral dimensions of each filament pair being substantially matched with respect to the lateral dimension of the lens body whereby both lens body and its centering means can be freely inserted along the insertion axis through the surgical incision, the filaments being substantially identical in size, shape and resiliency such that the lens when implanted has uniform quadrilateral support.

2. An intraocular lens according to claim 1 where the respective medial portions are contiguous at their intersection.

3. An intraocular lens according to claim 1 where each filament intersection is in alignment with the insertion axis.

4. An intraocular lens according to claim 1 where each filament intersection is engagable by a gripping tool for insertion or retraction of the lens.

5. An intraocular lens according to claim 2 where each filament intersection is engagable by a tool-applied tension to cause the distal portions to come together.

6. An intraocular lens according to claim 2 where each filament intersection is engageable by a tool-applied compression to cause the distal portions to spread apart.

7. An intraocular lens according to claim 1 wherein the distal portion of the filament pairs are co-planar.

8. An intraocular lens according to claim 1 where the distal portions of the filament pairs are each configured in a arcuate segment that is congruent with the equitorial curvature of the eye angle.

9. An intraocular lens according to claim 1 where the filament pairs have posterior angulation such that the implanted lens provides a posterior vault space between the lens body and the iris.

10. A method of implanting an anterior chamber intraocular lens comprising the steps of providing a lens according to claim 1, grasping the lens body and by probe-applied tensioning force at least one filament pair at points in alignment with the insertion axis, and inserting the thus grasped lens through a surgical incision into the anterior chamber in a plane generally parallel to and with vault spacing from the iris plane.

11. A method of implanting an anterior chamber intraocular lens according to claim 10, comprising the step of manipulating at least one of the opposed filament pairs by a tool applied to its intersection to cause the distal ends of the filament pair to be brought together or spread apart for quadrilateral support within the eye angle.

12. A method of implanting an anterior chamber intraocular lens according to claim 11, comprising the steps of centering the lens body in the chamber and fitting the distal ends within the eye angle under a state of compression sufficient to maintain centration of the lens body.

* * * * *

UNITED STATES PATENT AND TRADEMARK OFFICE
CERTIFICATE OF CORRECTION

PATENT NO. : 4,581,032

DATED : April 8, 1986

INVENTOR(S) : Stanley C. Grandon

It is certified that error appears in the above-identified patent and that said Letters Patent is hereby corrected as shown below:

Column 1, line 32 "disigned" should be --designed--.

Column 2, line 17 "is" second occurrence should be --in--.

Column 2, line 39 "ia" should be --is--.

Column 4, line 14 "appled" should be --applied--.

Signed and Sealed this

Nineteenth Day of August 1986

[SEAL]

Attest:

DONALD J. QUIGG

Attesting Officer

Commissioner of Patents and Trademarks